United States Patent [19]

Hata et al.

[11] Patent Number: 5,683,716

[45] Date of Patent: Nov. 4, 1997

[54] ENCAPSULATED MEDICINE

[75] Inventors: Takehisa Hata, Nagaokakyo; Fumio Shimojo, Kawanishi; Kazutake Kado, Toyonaka; Kyoko Ishii, Osaka; Seiji Sawai, Takarazuka, all of Japan

[73] Assignee: Fujisawa Pharmaceutical Co., Ltd., Osaka, Japan

[21] Appl. No.: 569,122

[22] PCT Filed: Jun. 28, 1994

[86] PCT No.: PCT/JP94/01043

§ 371 Date: Jan. 2, 1996

§ 102(e) Date: Jan. 2, 1996

[87] PCT Pub. No.: WO95/01166

PCT Pub. Date: Jan. 12, 1995

[30] Foreign Application Priority Data

Jun. 30, 1993 [JP] Japan .................................. 5-160983

[51] Int. Cl.$^6$ ........................... A61K 9/48; A61K 31/44
[52] U.S. Cl. ........................... 424/451; 424/461; 424/464
[58] Field of Search ........................... 424/451, 450; 514/406, 772.7

[56] References Cited

U.S. PATENT DOCUMENTS 5,340,591  8/1994  Nakano et al. ........................ 424/499

FOREIGN PATENT DOCUMENTS 0278166  11/1987  European Pat. Off. .

Primary Examiner—Thurman K. Page
Assistant Examiner—Sharon Howard
Attorney, Agent, or Firm—Oblon, Spivak, McClelland, Maier & Neustadt, P.C.

[57] ABSTRACT

This invention relates to an encapsulated pharmaceutical dosage form comprising a practically insoluble compound or salt and an intracapsular fluid, and/or a surfactant and/or cellulose derivative. It provides for increased oral absorption as compared with the conventional system because, on release of capsule contents from the capsule shell, the practically insoluble compound or salt undergoes diminution in crystal size.

12 Claims, No Drawings

ENCAPSULATED MEDICINE

TECHNICAL FIELD

This invention relates to an encapsulated pharmaceutical composition comprising a practically insoluble compound or a salt thereof and an intracapsular fluid, and/or a surfactant and/or cellulose derivative and finds application in the medical field.

BACKGROUND ART

Being very poorly soluble in water, the so-called practically insoluble compounds are generally absorbed only sparingly on oral administration in a crystalline or finely divided powder form and much research has been undertaken for improving their absorption. As typically disclosed in Japanese Patent Application Kokai H-5-17356, there is known a hard capsule containing a liquid composition comprising nifedipine, which is a practically insoluble compound, polyethylene glycol and polyvinylpyrrolidone. In this prior art invention, polyvinylpyrrolidone is added for improving the solubility of the drug in water.

Heretofore, various absorption-improving agents for practically insoluble compounds have been explored for the purpose of preventing precipitation of such practically insoluble compounds or increasing their solubility in the gastrointestinal tract. However, the technologies so far proposed at times fail to provide for satisfactory improvements in absorption and the advent of new absorption-improving agents for practically insoluble compounds has been awaited.

DISCLOSURE OF INVENTION

The inventors of this invention explored a quite new pharmaceutical approach by which the process of precipitation after release of contents of a capsule comprising a practically insoluble compound can be controlled to provide microcrystals in situ and found that a capsule comprising a practically insoluble compound or a salt thereof and an intracapsular fluid, and/or a surfactant and/or cellulose derivative provides for high bioavailability of the compound after oral administration. This invention has been developed on the basis of the above finding.

The practically insoluble compound for use in this invention is a compound having an extremely low solubility in water and, as such, showing poorly oral absorption kinetics. As examples of the compound, nilvadipine, 3-(difluoromethyl)-1-(4-methoxyphenyl)-5-(4-methylsulfonylphenyl)pyrazole, and 3-(difluoromethyl)-1-(4-methoxyphenyl)-5-(4-methylsulfinylphenyl)pyrazole can be mentioned.

The intracapsular fluid for use in this invention is a fluid which is conventionally used in soft capsules and, as such, includes polyhydric alcohols such as polyethylene glycol, propylene glycol, butylene glycol, polypropylene glycol, glycerol, polyglycerol, etc. and oils/fats such as fatty acid glycerol esters, sesame oil, soybean oil and so on.

Of them, polyhydric alcohols are preferred and polyethylene glycol is more recommendable, and polyethylene glycol 400 is the most advantageous.

The surfactant for use in this invention includes nonionic surfactants which are conventionally used in the art. Preferred are polyalcohol ester surfactants and the most useful is polyoxyl stearate.

The cellulose derivative for use in this invention includes hydroxypropylcellulose, hydroxypropylmethylcellulose, methylcellulose and carboxymethylcellulose, among other derivatives. Of them, the preferred is hydroxypropylcellulose, the more recommendable is a medium-or low-degree-of-polymerization hydroxypropylcellulose, and the most advantageous is a low-degree-of-polymerization hydroxypropylcellulose.

The pharmaceutical dosage form of this invention may, where necessary, contain those common additives which are conventionally used in pharmaceutical practice (e.g. corrigents, perfumes, etc.). The optimal dosage form is a soft capsule or a hard capsule.

The process for producing the dosage form of this invention employing a practically insoluble compound or a salt thereof and an intracapsular fluid, and/or a surfactant and/or cellulose derivative is now described in detail.

The pharmaceutical dosage form of this invention can be manufactured by mixing a practically insoluble compound or a salt thereof, with an intracapsular fluid, and/or a surfactant and/or cellulose derivative, plus other conventional additives where necessary, and processing the resultant mixture into the desired dosage form in the conventional manner.

By the procedure described above, a pharmaceutical dosage form comprising a practically insoluble compound or a salt thereof and an intracapsular fluid, and/or a surfactant and/or cellulose derivative according to this invention can be provided. For this manufacturing process, the kinds and amounts of intracapsular fluid, surfactant, cellulose derivative and additives can be judiciously selected according to the intended dosage form, the required dose of the practically insoluble compound to be contained and the desired pattern and duration of release of the practically insoluble compound, among other factors.

The preferred formulation according to this invention is the combination of a practically insoluble compound or a salt thereof, an intracapsular fluid and a surfactant, or the combination of a practically insoluble compound or a salt thereof, an intracapsular fluid and a cellulose derivative.

The proportions of the respective components of this invention can be judiciously selected according to the designed kinetics of release of the practically insoluble compound. Generally speaking, the preferred proportions based on unity of the practically insoluble compound or salt thereof are about 5~99.5 for the intracapsular internal fluid, about 0.05~10 for the surfactant and about 0.05~20 for the cellulose derivative.

The following examples are intended to describe this invention in further detail.

EXAMPLE 1

A solution of 3-(difluoromethyl)-1-(4-methoxyphenyl)-5-(4-methylsulfonylphenyl)pyrazole (1.4 g) in PEG-400 (Sanyo Chemical Industries, Ltd., generic name: polyethylene glycol 400) (16.6 g) is mixed with TC-5R (Shin-Etsu Chemical Co., Ltd., generic name: hydroxypropylmethylcellulose) (2.0 g) and the mixture is filled into No. 4 hard capsule shells to provide capsules. The composition per capsule is as follows.

| | |
|---|---|
| 3-(Difluoromethyl)-1-(4-methoxyphenyl)-5-(4-inethyisulfonylphenyl)pyrazole | 14 mg |
| PEG-400 | 166 mg |
| TC-5R | 20 mg |
| | 200 mg |

EXAMPLE 2

A solution of 3-(difluoromethyl)-1-(4-methoxyphenyl)-5-(4-methylsulfonylphenyl)pyrazole (1.4 g) in PEG-400 (18.4 g) is mixed with HPC-L (Shin-Etsu Chemical Co., Ltd., generic name: low-degree-of-polymerization hydroxypropylcellulose) (0.2 g) and the mixture is filled into No. 4 hard capsule shells to provide capsules.

The composition per capsule is as follows.

| | |
|---|---|
| 3-(Difluoromethyl)-1-(4-methoxyphenyl)-5-(4-methylsulfonylphenyl)pyrazole | 14 mg |
| PEG-400 | 184 mg |
| HPC-L | 2 mg |
| | 200 mg |

EXAMPLE 3

A solution of 3-(difluoromethyl)-1-(4-methoxyphenyl)-5-(4-methylsulfonylphenyl)pyrazole (1.4 g) in PEG-400 (17.6 g) is mixed with HPC-L (1.0 g) and the mixture is filled into No. 4 hard capsule shells to provide capsules.

The composition per capsule is as follows.

| | |
|---|---|
| 3-(Difluoromethyl)-1-(4-methoxyphenyl)-5-(4-methylsulfonylphenyl)pyrazole | 14 mg |
| PEG-400 | 176 mg |
| HPC-L | 10 mg |
| | 200 mg |

EXAMPLE 4

The procedure of Example 2 is repeated using MYS-40 (Nikko Chemicals Co., Ltd., generic name: polyoxyl stearate 40) in lieu of HPC-L to provide capsules.

The composition per capsule is as follows.

| | |
|---|---|
| 3-(Difluoromethyl)-1-(4-methoxyphenyl)-5-(4-methylsulfonylphenyl)pyrazole | 14 mg |
| PEG-400 | 184 mg |
| MYS-40 | 2 mg |
| | 200 mg |

EXAMPLE 5

A solution of nilvadipine (5 g) in PEG-400 (85 g) is mixed with HPC-L (10 g) and the mixture is filled into No. 4 hard capsule shells to provide capsules.

The composition per capsule is as follows.

| | |
|---|---|
| Nilvadipine | 10 mg |
| PEG-400 | 170 mg |
| HPC-L | 20 mg |
| | 200 mg |

[Effect of Invention]

The pharmaceutical dosage form of this invention provides for high bioavailability and sustained action after oral administration because when the capsule contents comprising a practically insoluble compound are released from the capsule, the practically insoluble compound undergoes diminution in crystal size.

To demonstrate the above effect, the results of an in vitro particle size distribution test and an oral absorption test in dogs, both conducted using some representative pharmaceutical compositions according to this invention are shown below.

Particle size distribution test (1) Test pharmaceutical compositions

Capsule contents 1: Capsule contents of the composition according to Example 1.

Capsule contents 2: Capsule contents of the composition according to Example 2.

Capsule contents 3: Capsule contents of the composition according to Example 3.

Capsule contents 4: Capsule contents of the composition according to Example 4.

Capsule contents 5: Capsule contents of the composition according to Example 5.

Control capsule contents A: Capsule contents obtained by dissolving 3-(difluoromethyl)-1-(4-methoxyphenyl)-5-(4-methylsulfonylphenyl)pyrazole (70 mg) in PEG-400 (930 mg).

Control capsule contents B: Capsule contents obtained by dissolving nilvadipine (50 mg) in PEG-400 (950 mg).

(2) Method

A double-walled glass tube was filled with 10 ml of distilled water and at a constant temperature of 37° C., 0.1 ml of each test capsule contents was added. After 3 hours of stirring, the distribution of solid phase particle size was determined. The results were expressed in mean particle diameter.

Instrument: Laser light scattering type particle size analyzer LDSA-2300A (Tonichi Computer Applications, Ltd.)

Measuring conditions: focus—100 μm Determined in triplicate (3) Results

| Test capsule contents | Mean particle diameter (μm) |
|---|---|
| Capsule contents 1 | 13.7 |
| Capsule contents 2 | 8.3 |
| Capsule contents 3 | 6.5 |
| Capsule contents 4 | 20.6 |
| Capsule contents 5 | 4.6 |
| Control capsule contents A | 48.2 |
| Control capsule contents B | 34.8 |

The above particle size distribution test made it clear that compared with the capsule contents comprising the practically insoluble compound and intracapsular fluid, the capsule contents comprising the practically insoluble compound and intracapsular fluid, and/or surfactant and/or cellulose derivative give finer crystals on release in water.

Since an improvement in oral absorption could be expected from the above results, the following experiment was performed.

Oral absorption test (1) Test pharmaceutical compositions

The capsule contents 1–4 and control capsule contents A used in the particle size distribution test were respectively filled into hard capsule shells (referred to as capsules 1–4 and control capsule A, respectively) and the filled capsules were used in the test.

(2) Method

Using 3 male beagle dogs (body weights 8.5~10.5 kg) fasted overnight, the above samples were administered to the same dogs at 1-week intervals.

Each composition was filled into hard capsule shells at the ratio of 2 mg/kg of 3-(difluoromethyl)-1-(4-methoxyphenyl)-5-(4-methylsulfonylphenyl)pyrazole and the filled capsules were administered by the oral route. After administration, the blood was collected serially from the antebrachial vein and the plasma concentration of 3-(difluoromethyl)-1-(4-methoxyphenyl)-5-(4-methylsulfonylphenyl)pyrazole was determined by HPLC.

(3) Results

The data on maximum plasma concentration ($C_{max}$), area under the plasma concentration-time curve ($AUC_{0-24}$) and bioavailability (BA) after oral administration are shown in the following table. Each value is the mean ± standard error.

| Test dosage form | $C_{max}$ (μg/ml) | $AUC_{0-24}$ (μgÅhr/ml) | BA (%) |
|---|---|---|---|
| Capsule 1 | 0.188 ±0.004 | 0.983 ±0.249 | 45.0 |
| Capsule 2 | 0.261 ±0.906 | 1.057 ±0.204 | 49.1 |
| Capsule 3 | 0.420 ±0.096 | 1.421 ±0.349 | 65.6 |
| Capsule 4 | 0.447 ±0.292 | 1.200 ±0.364 | 39.5 |
| Control capsule A | 0.096 ±0.002 | 0.445 ±0.087 | 20.7 |

It is clear from the above oral absorption test data that the pharmaceutical dosage form of this invention is much more orally absorbable than the dosage form comprising only 3-(difluoromethyl)-1-(4-methoxyphenyl)-5-(4-methylsulfonylphenyl)pyrazole and intracapsular fluid.

The above test results further indicate that unlike the conventional dosage form comprising a practically insoluble compound and an intracapsular fluid intended for preventing precipitation or increasing solubility in the gastrointestinal tract, the capsule of this invention comprising a practically insoluble compound or a salt thereof and an intracapsular fluid, and/or a surfactant and/or cellulose derivative provides for better oral absorption because of the diminution of crystal size in the gastrointestinal tract. Thus, this invention is a very useful oral absorption-improving system for practically insoluble compounds.

We claim:

1. An encapsulated pharmaceutical dosage form, comprising a practically insoluble compound or salt thereof, an intracapsular fluid, and a compound selected from the group consisting of hydroxypropylcellulose, hydroxypropylmethylcellulose, methylcellulose and carboxymethylcellulose, said dosage form forming microcrystals in situ having a mean particle diameter of no more than about 20.6 μm.

2. The pharmaceutical dosage form of claim 1, wherein said intracapsular fluid is a polyhydric alcohol, fatty acid glycerol ester, sesame oil or soybean oil.

3. The pharmaceutical dosage form of claim 2, wherein said polyhydric alcohol is selected from the group consisting of polyethylene glycol, propylene glycol, butylene glycol, polypropylene glycol, glycerol and polyglycerol.

4. The pharmaceutical dosage form of claim 1, which contains hydroxypropyl cellulose.

5. The pharmaceutical dosage form of claim 3, wherein said polyethylene glycol is polyethylene glycol 400.

6. The pharmaceutical dosage form of claim 1, wherein said practically insoluble compound is selected from the group consisting of 3-(difluoromethyl)-1-(4-methoxyphenyl)-5-(4-methylsulfonylphenyl)pyrazole and 3-(difluoromethyl)-1-4-methoxyphenyl)-5-(4-methylsulfiinylphenyl)pyrazole.

7. An encapsulated pharmaceutical dosage form, comprising a practically insoluble compound or salt thereof, and intracapsular fluid, a surfactant and a compound selected from the group consisting of hydroxypropylcellulose, hydroxypropylmethylcellulose, methylcellulose and carboxymethylcellulose.

8. The pharmaceutical dosage form of claim 7, wherein said intracapsular fluid is a polyhydric alcohol, fatty acid glycerol ester, sesame oil or soybean oil.

9. The pharmaceutical dosage form of claim 8, wherein said polyhydric alcohol is selected from the group consisting of polyethylene glycol, propylene glycol, butylene glycol, polypropylene glycol, glycerol and polyglycerol.

10. The pharmaceutical dosage form of claim 9, wherein said polyhydric alcohol is polyethylene glycol and said compound is hydroxypropylcellulose.

11. The pharmaceutical dosage form of claim 10, wherein said polyethylene glycol is polyethylene glycol 400.

12. The pharmaceutical dosage form of claim 11, wherein said practically insoluble compound is selected from the group consisting of 3-difluoromethyl)-1-(4-methoxyphenyl-5-(4-methylsulfonylphenyl)pyrazole and 3-(difluoromethyl)- 1-(4-methoxyphenyl)-5-(4 methylsulfonylphenyl)pyrazole.

* * * * *